US00PP30713P2

(12) United States Plant Patent
Trees

(10) Patent No.: US PP30,713 P2
(45) Date of Patent: Jul. 16, 2019

(54) ***IBERIS* PLANT NAMED 'SUMMER SNOWDRIFT'**

(50) Latin Name: *Iberis hybrid*
Varietal Denomination: Summer Snowdrift

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/999,971

(22) Filed: Sep. 4, 2018

(51) Int. Cl.
*A01H 5/02* (2018.01)
*A01H 6/20* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Iberis* plant named 'Summer Snowdrift', characterized by its pure white-colored flowers, dark green-colored foliage, and moderately vigorous, mounded-spreading growth habit, is disclosed.

1 Drawing Sheet

Latin name of genus and species of plant claimed: *Iberis* hybrid.

Variety denomination: 'Summer Snowdrift'.

BACKGROUND OF THE INVENTION

The present invention relates to a new and distinct cultivar of *Iberis* plant botanically known as *Iberis* hybrid and hereinafter referred to by the cultivar name 'Summer Snowdrift'.

The new cultivar originated in a controlled breeding program in Guadalupe, Calif. The objective of the breeding program was the development *Iberis* cultivars that have high heat tolerance and a long flowering season.

The new *Iberis* cultivar is a colchicine-induced sport of is the proprietary *Iberis* hybrid breeding selection coded 16336, not patented, characterized by its pure white-colored flowers, dark green-colored foliage, and moderately vigorous, mounded-spreading growth habit. The colchicine treatment occurred in March 2013. The new cultivar was discovered as a side shoot and selected during July 2014 in a controlled environment in Guadalupe, Calif.

Asexual reproduction of the new cultivar by terminal stem cuttings since July 2014 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Summer Snowdrift' as a new and distinct cultivar of *Iberis* plant:

1. Pure white-colored flowers;
2. Dark green-colored foliage; and

3. Moderately vigorous, mounded-spreading growth habit.

Plants of the new cultivar differ from plants of the parent primarily in having a larger flower diameter, slightly darker green-colored foliage, and in continuing to freely flower even under high heat conditions.

Of the many commercially available *Iberis* cultivars, the most similar in comparison to the new cultivar is 'White Heat', U.S. Plant Pat. No. 28,674. However, in side by side comparisons, plants of the new cultivar differ from plants of 'White Heat' in at least the following characteristics:

1. Plants of the new cultivar have larger flowers than plants of 'White Heat';
2. Plants of the new cultivar have more flowers per terminal corymb than plants of 'White Heat'; and
3. Plants of the new cultivar have a more branches than plants of 'White Heat'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Summer Snowdrift'. The plants were approximately four months old. The plants were grown in one-gallon containers for approximately 11 weeks in a greenhouse in Elburn, Ill. Plants were given two pinches, one at one week before transplant and one two weeks after transplant.

DETAILED BOTANICAL DESCRIPTION

Figure 1:
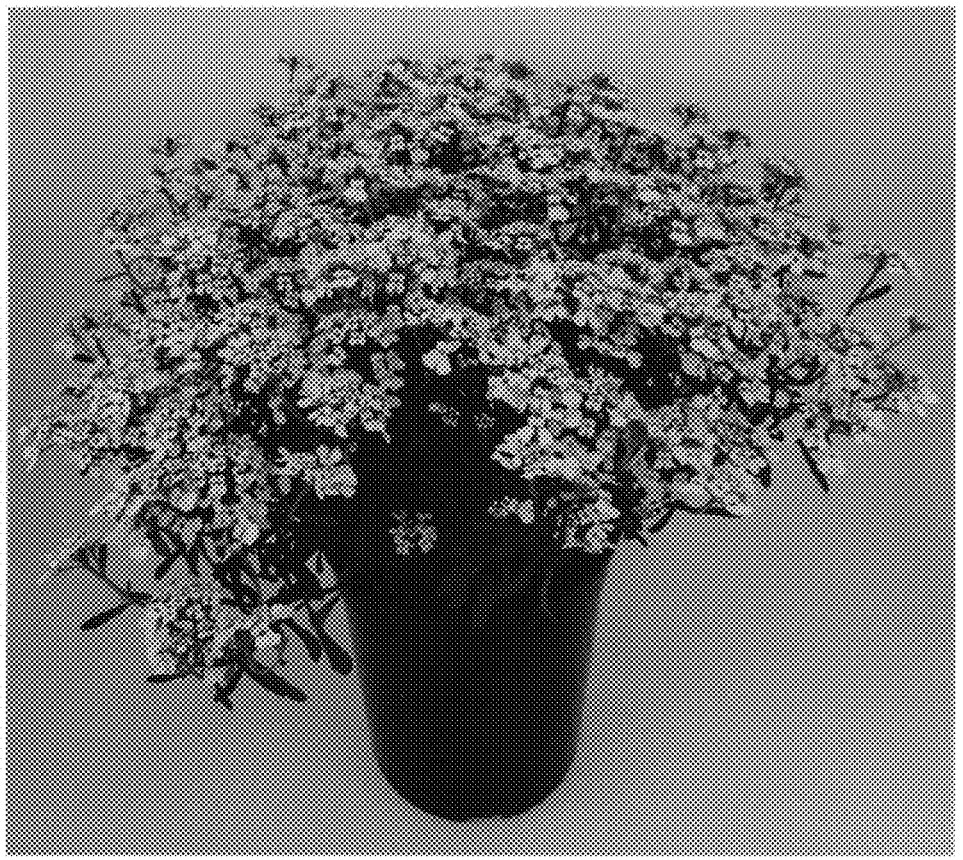
FIG. 1 illustrates a side view of the overall growth and flowering habit of 'Summer Snowdrift'.
Figure 2:
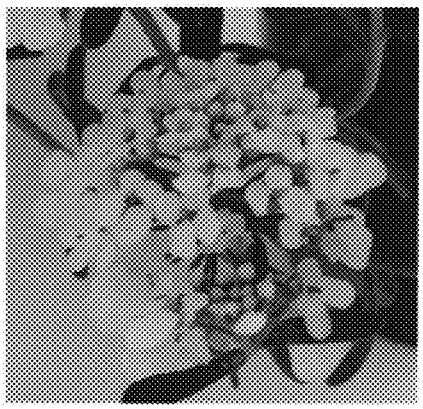
FIG. 2 illustrates a close-up view of the inflorescences of 'Summer Snowdrift'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2018 under natural light conditions in West Chicago, Ill.

The following descriptions and measurements describe approximately four-month old plants produced from cuttings from stock plants and grown under conditions comparable to those used in commercial practice. The plants were grown in one-gallon containers for approximately 11 weeks in a greenhouse in Elburn, Ill. Plants were given two pinches, one at one week before transplant and one two weeks after transplant. Greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Iberis* hybrid 'Summer Snowdrift'.

Parentage:

*Parent*.—Proprietary *Iberis* hybrid breeding selection coded 16336, not patented Propagation:

*Type cutting*.—Terminal stem.

*Time to initiate roots*.—Approximately 12 to 14 days.

*Time to produce a rooted cutting*.—Approximately 14 to 28 days.

*Root description*.—Fine, fibrous.

*Rooting habit*.—Freely branching.

Plant description:

*Commercial crop time*.—Approximately 10 to 12 weeks from a rooted cutting to finish in a 15 cm pot.

*Growth habit and general appearance*.—Herbaceous tender perennial, moderately vigorous, mounded-spreading.

*Hardiness*.—USDA Zone 6b (—5° F. to 0° F./−20.6° C. to −17.8° C.).

*Size*.—Height from soil level to top of plant plane: Approximately 24.5 cm. Width: Approximately 42.0 cm.

*Branching habit*.—Freely branching, pinching improves later branching. Quantity of main branches per plant: Approximately 12.

*Branch*.—Shape: Ribbed. Strength: Strong. Length: Approximately 16.0 cm. Diameter: Approximately 4.0 mm. Length of central internode: Approximately 9.0 mm. Texture: Ridged and moderately pubescent. Color of young stems: 146C. Color of mature stems: 146B, becoming woody 199B with age.

Foliage description:

*General description*.—Quantity of leaves per main branch: Approximately 15. Fragrance: None detected. Form: Simple. Arrangement: Alternate.

*Leaves*.—Aspect: Perpendicular or obtuse angle to stem. Shape: Spatulate. Margin: Dentate, ciliate. Apex: Broadly acute to rounded. Base: Attenuate, sessile. Venation pattern: Pinnate. Length of mature leaf: Approximately 4.5 cm. Width of mature leaf: Approximately 1.0 cm. Texture of upper and lower surfaces: Glabrous, leathery. Color of upper surface of young and mature foliage: 137A, venation indistinguishable. Color of lower surface of young and mature foliage: 137C, midvein 146D other venation indistinguishable.

Flowering description:

*Flowering habit*.—'Summer Snowdrift' is freely flowering under outdoor growing conditions with substantially continuous blooming from spring through autumn.

*Lastingness of individual flower on the plant*.—Approximately 5 to 7 days.

Inflorescence description:

*General description*.—Type: Corymb. Quantity per plant: Approximately 180. Fragrance: Slight. Length or height of terminal corymb: Approximately 3.0 cm. Width of terminal corymb: Approximately 4.0 cm. Length or height of axillary corymb: Approximately 1.5 cm. Width of axillary corymb: Approximately 3.5 cm. Quantity of fully open flowers per terminal corymb: Approximately 30. Quantity of fully open flowers per axillary corymb: Approximately 13.

*Peduncle*.—Strength: Strong. Aspect: Primary erect, axillary acute angle to stem. Length of primary: Approximately 1.5 cm. Diameter of primary: Approximately 2.5 mm. Length of axillary: Approximately 1.5 cm to 2.0 cm. Diameter of axillary: Approximately 2.0 mm. Texture: Moderately pubescent. Color: Closest to 146A.

Flower description:

*Type*.—Small, asymmetrical cruciferous flowers with two larger abaxial pairs of petals and two smaller adaxial pairs, freely flowering, not persistent, facing outwardly to upright.

*Bud*.—Rate of opening: Generally takes 3 to 4 days for bud to progress from first color to fully open flower.

*Bud just before opening*.—Shape: Globose. Diameter: Approximately 3.0 mm. Color: Sepal centers of 144A and margins of NN155D; petals of NN155D.

*Corolla*.—Shape: Cruciform lobes with claws surrounded by calyx. Aspect: Facing upward and outward. Length: Approximately 1.0 cm. Width: Approximately 1.1 cm.

*Petals*.—Quantity: 4. Shape: Obovate. Margin: Entire. Apex: Obtuse. Base: Attenuate. Length of abaxial lobe: Approximately 7.0 mm. Width of abaxial lobe: Approximately 5.0 mm. Length of adaxial lobe: Approximately 3.0 mm. Width of adaxial lobe: Approximately 3.0 mm. Length of claw: Approximately 2.0 mm. Width of claw: Less than 1.0 mm. Color of upper surface of lobe when first and fully open: NN155D. Color of lower surface of lobe when first and fully open: NN155D. Color of upper and lower surfaces of claw: Lighter than 145D.

*Calyx*.—Shape: Cupped. Diameter: Approximately 4.0 mm.

*Sepals*.—Quantity per flower: 4, distinct. Shape: Elliptic. Apex: Obtuse. Base: Truncate. Length: Approximately 3.0 mm. Width: Approximately 2.0 mm. Texture of inner and outer surfaces: Glabrous. Color of inner and outer surfaces: Centers of 144A to 144B and margins of NN155D.

*Pedicel*.—Strength: Strong, flexible. Aspect: Acute angle to stem. Length: Approximately 1.0 cm. Diameter: Approximately 1.0 mm. Texture: Adaxial surface densely glandular pubescent. Color: Closest to 146A.

*Reproductive organs*.—Androecium: Stamen quantity: 6 per flower. Stamen length: Approximately 3.0 mm, 1 pair slightly shorter and inserted lower. Filament color: 145C tinted with 83A. Anther shape: Sagittate, dorsifixed. Anther color: 13C. Pollen amount: Not observed. Gynoecium: Pistil quantity: 1 per flower, ovary superior, flattened orbicular. Pistil length: Approximately 4.0 mm. Stigma shape: Bifid. Stigma color: 144A. Style length: Approximately 2.0 mm. Style color: 144A. Ovary diameter: Approximately 2.0 mm. Ovary color: 145B.

Seed and fruit production: Neither seed nor fruit production has been observed.

Disease and pest resistance: Resistance to pathogens and pests common to *Iberis* has not been observed.

What is claimed is:

1. A new and distinct cultivar of *Iberis* plant named 'Summer Snowdrift', substantially as herein illustrated and described.

* * * * *